United States Patent [19]

Friese et al.

[11] Patent Number: 5,098,549
[45] Date of Patent: Mar. 24, 1992

[54] SENSOR ELEMENT FOR LIMITING CURRENT SENSORS FOR DETERMINING THE λ VALUE OF GAS MIXTURES

[75] Inventors: Karl-Hermann Friese, Leonberg; Werner Grünwald, Gerlingen, both of Fed. Rep. of Germany

[73] Assignee: Robert Bosch GmbH, Stuttgart, Fed. Rep. of Germany

[21] Appl. No.: 490,667

[22] PCT Filed: Aug. 20, 1988

[86] PCT No.: PCT/DE88/00512

§ 371 Date: Feb. 27, 1990

§ 102(e) Date: Feb. 27, 1990

[87] PCT Pub. No.: WO89/02074

PCT Pub. Date: Mar. 9, 1989

[30] Foreign Application Priority Data

Aug. 27, 1987 [DE] Fed. Rep. of Germany ....... 3728618

[51] Int. Cl.⁵ .................................................. G01N 27/56
[52] U.S. Cl. .................................. 204/425; 204/424; 204/426
[58] Field of Search ........................ 204/424, 425, 426

[56] References Cited

U.S. PATENT DOCUMENTS

| 4,450,065 | 5/1984 | Yamada | 204/412 |
| 4,505,807 | 3/1985 | Yamada | 204/425 |

FOREIGN PATENT DOCUMENTS

| 0142993 | 5/1985 | European Pat. Off. |
| 0188900 | 7/1986 | European Pat. Off. |
| 0194082 | 9/1986 | European Pat. Off. |
| 3632456 | 4/1987 | Fed. Rep. of Germany |
| 0011530 | 5/1980 | France |

*Primary Examiner*—John Niebling
*Assistant Examiner*—William T. Leader
*Attorney, Agent, or Firm*—Michael J. Striker

[57] ABSTRACT

A sensor element for limiting current sensors for determining the λ value of gas mixtures is proposed which has two interconnected inner pump electrodes (8 and 8') disposed opposite each other in a diffusion channel (7). The resulting increase of the effective surface at the beginning of the inner electrodes markedly reduces the disadvantageous electrode polarization which occurs in sensor elements having only one inner pump electrode. At the same time, a better utilization of the noble metal required to form the pump electrodes is achieved.

8 Claims, 1 Drawing Sheet

SENSOR ELEMENT FOR LIMITING CURRENT SENSORS FOR DETERMINING THE λ VALUE OF GAS MIXTURES

BACKGROUND OF THE INVENTION

The invention is based on a sensor element for limiting current sensors for determining the λ value of gas mixtures, particularly of exhaust gases of internal combustion engines. In such sensor elements, which employ the principle of the diffusion limiting current, the limiting current is measured at a constant voltage applied to both electrodes of the sensor element. In exhaust gas produced in combustion processes, this current is dependent on the oxygen concentration as long as the diffusion of the gas to the pump electrode determines the rate of the reaction occurring. It is known to construct such sensors employing the polarographic principle of measurement in a manner such that both the annode and the cathode are exposed to the gas to be measured, the cathode having a diffusion barrier in order to achieve operation in the region of the diffusion limiting current.

The known limiting current sensors serve, as a rule, to determine the λ value of gas mixtures, which denotes the "total oxygen/oxygen required for complete combustion of the fuel" ratio of an air/fuel mixture combusting in a cylinder. The sensors determine the oxygen content of the exhaust gas by a change in electrochemical potential.

Owing to a simplified and cheap method of manufacture, the manufacture of sensor elements produced by ceramic-film and screen-printing technology has become established in practice in recent years.

In a simple and efficient manner, planar sensor elements can be produced on the basis of planar solid electrolytes or oxygen-conducting solid electrolytes in the form of a film, for example, from stabilized zirconium dioxide, which are coated on both sides with one inner and outer pump electrode each, having the associated conductor tracks. At the same time, the inner pump electrode is advantageously disposed in the peripheral region of a diffusion channel through which the gas under test is supplied and which serves as a gas diffusion resistor.

From German Offenlegungsschrift 3,543,759 and also EP-A-O, 142,993, O, 188,900 and O, 194,082, sensor elements and detectors are furthermore known which have in common the fact that they each have a pump cell and a sensor cell which comprise planar solid electrolytes or oxygen-conducting solid electrolytes in the form of a film and two electrodes disposed thereon and have a common diffusion channel.

A disadvantage of the prior art sensor elements is that the front section, facing the gas under test, of the inner pump electrode is subjected to a severer load than the rear section facing away from the gas under test. This results in a high electrode polarisation which requires a high pump voltage. The latter in turn entails the danger of an electrolyte decomposition in the region of the inner pump electrode.

SUMMARY OF THE INVENTION

According to the invention, the sensor element formed as a pump cell for a limiting current sensor for determining the λ value of lean exhaust gas of an internal combustion engine, comprises a planar solid electrolyte or solid electrlyte in the form of a film, which conducts $O^{2-}$ ions and is formed with a diffusion channel for the gas under test, an outer pump electrode disposed on the solid electrolyte and connected to a first conductor track, and two inner pump electrodes arranged in the diffusion channel opposite the outer pump electrode and on opposite sides of the diffusion channel, the inner pump electrodes being directly connected one to another and to a second conductor track extending into the diffusion channel.

In contrast to this, the sensor element according to the invention having an outer pump electrode and two interconnected inner pump electrodes arranged opposite each other in the diffusion channel, has the advantage that the effective surface of the inner pump electrode is increased at the beginning of the electrode and the necessity of increasing the pump voltage does not arise. The extension of the area of the pump electrode into the depth of the diffusion channel can remain correspondingly low. The invention consequently makes possible a better exploitation of the quantity of noble metal, for example platinum, needed to form the pump electrodes. A reduced drop in the limiting current furthermore occurs with increasing electrode ageing compared with the conventional arrangement of the inner pump electrode on only one side of the diffusion channel.

The sensor element according to the invention can be used instead of known sensor elements of planar structure in limiting current sensors of standard design. In this connection, broad-band sensors (λ 1) and lean sensors (λ>1) are suitable. The sensors according to the invention may consequently be formed only as a pump cell, possibly with a heating element, for example as a lean sensor for diesel engines and incorporated as such in a standard sensor housing, for example of the type known from German Offenlegungsschrift 3,206,903 and 3,537,051 and used to measure the fuel/air ratio in a lean or rich exhaust gas. In addition to the pump cell, the sensor element according to the invention may also have, in addition, a sensor cell (Nernst cell) which is provided with an additional air reference channel and one electrode of which is disposed in the region of the pump electrode in the diffusion channel of the pump cell and the other electrode of which is situated in the air reference channel.

In another embodiment of the sensor element of the invention, the inner pump electrodes can be mounted on different solid electrolytes assembled by a laminating process. Advantageously, an insulating layer is disposed between the first conductor track and the solid electrolyte on which it is mounted. This sensor element can also have a heater contained between two additional solid electrolytes assembled by a lamination process.

A porous covering layer is advantageously provided above the outer pump electrode and the associated conductor track.

In another embodiment of the invention, the inner pump electrodes and the outer pump electrode are annular electrodes. An inlet hole is provided in the solid electrolytes, which joins the diffusion channel and inlet hole passes through the annular inner pump electrode and the outer pump electrode.

The sensor element according to the invention is advantageously manufactured by ceramic-film and screen-printing technology.

The diffusion channel can contain a porous filling, which acts as a diffusion barrier.

BRIEF DESCRIPTION OF THE DRAWING

The objects, features and advantages of the present invention will now be illustrated in more detail by the following detailed description, reference being made to the accompanying drawing in which.

DETAILED DESCRIPTION OF THE PREFERRED EMBODIMENT

Figure 1:
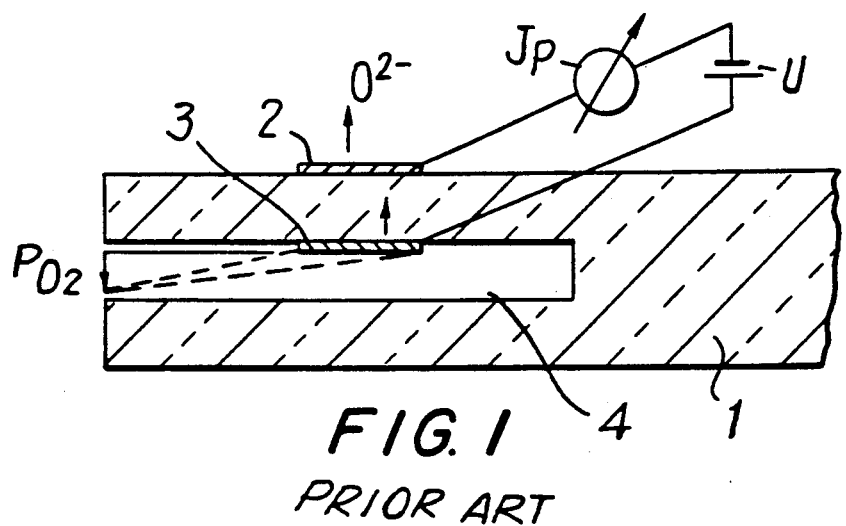
FIG. 1 is a diagrammatic cross-sectional view through a prior art sensor element including a planar solid electrolyte as carrier and an outer and inner pump electrode.

FIG. 1 shows the operating principle of a prior art sensor element comprising a planar solid electrolyte 1 as carrier for the outer pump electrode 2 and the inner pump electrode 3, which is disposed in the diffusion channel 4. The pump electrodes 2 and 3 are connected by schematically illustrated conductor tracks to a source of constant voltage u, and the current density of $O^{2-}$ is determined by indicator ions $J_p$. The diagrammatic representation of the partial pressure $PO_2$ of oxygen vs current density of $O^{2-}$ ions reveals the severer loading of the inner electrode 3 at the side facing the opening of the diffusion channel 4, since the oxygen partial pressure drops with the depth of the electrode and the current density depends on the oxygen partial pressure.

Figure 2:
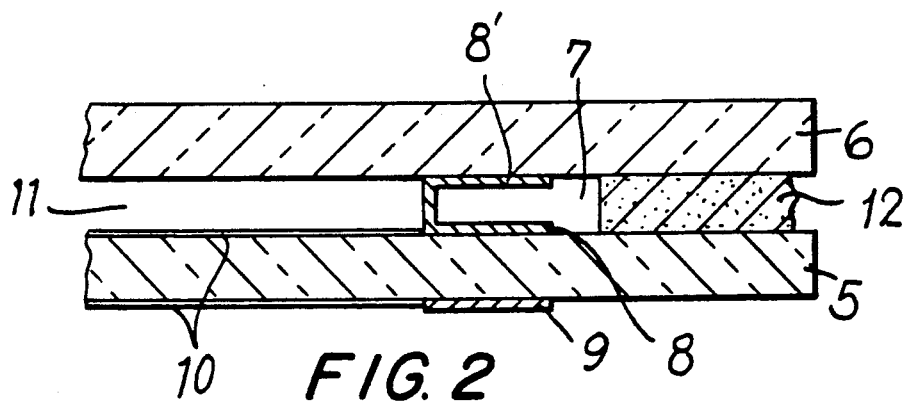
FIG. 2 is a diagrammatic cross-sectional view through a sensor element according to the invention including ceramic films on which the inner and outer pump electrodes have been printed.

FIG. 2 shows a sensor element according to the invention which can be manufactured by ceramicfilm and screen-printing technology. It comprises the solid electrolyte films 5 and 6 on which the inner pump electrodes 8 and 8' and also the outer pump electrode 9 have been printed together with the associated conductor tracks 10 and which are laminated together by a standard inter-lamina binder to form the diffusion channel 4 which comprises a tunnel. Advantageously, a porous filling 12 which serves as diffusion barrier for the gas under test has been provided, as shown, in the diffusion channel 7.

Figure 3:
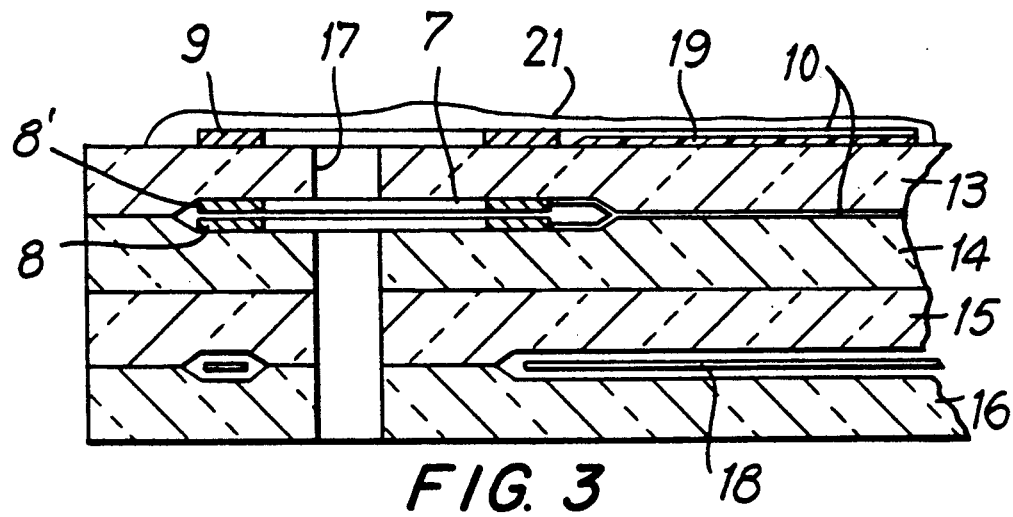
FIG. 3 is a diagrammatic cross-sectional view through another sensor element according to the invention, in which the inner pump electrodes and the outer pump electrodes are annularly disposed around the inlet for the gas under test.

FIG. 3 shows another advantageous embodiment of a sensor element according to the invention, which can be manufactured by ceramic-film and screen-printing technology and in which the inner pump electrodes 8 and 8' and also the outer pump electrode 9 are in this case annularly disposed around the inlet hole 17 for the gas under test. As shown in FIG. 3, the inlet hole 17 passes through the planar or film solid electrolytes 13, 14, 15, 16 and joins the diffusion channel 7. It is composed essentially of four solid electrolyte films 13, 14, 15 and 16 which have been laminated together and which have the punched-out inlet hole 17 of the diffusion channel 7 for the test gas, the annular outer pump electrode 9 and the two annular inner pump electrodes 8 and 8' which are disposed opposite each-other in the diffusion channel 7. The sensor element may furthermore have a heater 18. The films 15 and 16 with the heater are not, however, absolutely necessary. The annular electrodes 8, 8' and 9 exposed to the gas under test are connected to the conductor tracks 10, an insulating layer 19, for example an $Al_2O_3$ layer, being disposed beneath the conductor track 10. The conductor tracks are connected to a voltage source which is not shown, for example a battery having a constant working voltage in the range from 0.5 to 1.0 V. Advantageously, the outer pump electrode 9 and the associated conductor track 10 are covered by a porous covering layer 21, for example of magnesium spinel.

Suitable solid electrolytes which conduct oxygen ions for manufacturing sensor elements according to the invention are, in particular, those based on $ZrO_2$, $HfO_2$, $CeO_2$ and $ThO_2$. The use of laminae and films of yttrium-stabilized zirconium dioxide (YSZ) has proved to be particularly advantageous. At the same time the laminae and films have preferably a thickness of 0.25 to 0.3 mm.

The pump electrodes are preferably composed of a metal of the platinum group, in particular platinum, or of alloys of metals of the platinum group or alloys of metals of the platinum group with other metals. Advantageously, they contain a ceramic supporting structure material, for example, YSZ powder, having a proportion by volume of, preferably, about 40% by volume. They are porous and have a thickness of, preferably, 8 to 15 μm. The conductor tracks associated with the pump electrodes are composed, preferably, also of platinum or a platinum alloy of the type described. Pump electrodes and conductor tracks can be deposited by known methods on the solid electrolyte carrier, for example by screen printing. As a rule, there is an insulation layer, for example of $Al_2O_3$, between the conductor track connecting the outer pump electrode to a voltage source not shown in the drawing and the solid electrolyte film 13. It may, for example, have a thickness of about 15 μm. The individual films or laminae forming the sensor element can be joined together a method standard in ceramic-film and screen-printing technology in which the films are assembled and heated to temperatures of about 100° C. During this process the diffusion channel can be prepared at the same time. Advantageously, the latter is introduced using thick-layer technology, for example by a theobromine screen-printed area, the theobromine being evaporated during the subsequent sintering process. To produce the diffusion channel, use may also be made, for example, of thermal soot powders which burn out during the sintering process, or ammonium carbonate, which evaporates.

If the diffusion channel is to have a porous filling, instead of a theobromine screen-printed layer, it is possible to use, for example, a layer of theobromine or another vaporizable or combustible material and a material that still does not sinter compactly at the sintering temperature of the solid electrolyte substrate, for example coarse-grain $ZrO_2$, Mg spinel or $Al_2O_3$ with a grain size of, for example, 10 μm.

EXAMPLE

To produce the sensor element of the type shown diagrammatically in FIG. 3, films of yttrium-stabilized zirconium dioxide having a layer thickness of 0.3 mm were used. The pump electrodes, which are composed of platinum, were deposited on the carrier films by known screen-printing technology, a 20 μm thick $Al_2O_3$ insulation layer being deposited on the surface of the carrier films carrying the outer pump electrode in the region of the conductor track of the outer pump electrode beforehand. The annular pump electrodes had an outside diameter of 2.8 mm and an inside diameter of 1.4 mm, with a thickness of 12 μm. The conductor tracks were produced on the basis of a standard Pt Cermet paste composed of 85 parts by weight of Pt powder and 15 parts by weight of YSZ powder. The diffusion channel was introduced using thick-layer technology by means of a theobromine screen-printed layer, the theobromine being evaporated in the temperature range around 300° C. to leave behind an annular gap about 30 μm high and 1.3 mm deep. The central inlet opening for the gas under test had a diameter of 0.25 mm. After printing the carrier films, ie. after depositing the electrodes, conductor tracks, insulating layer and also, possibly, a covering layer on the outer pump electrode, the films were subjected after assembly to a sintering process in which they were heated for about 3 hours at a temperature in the region of 1380° C.

To manufacture a further sensor element with a heater, as shown diagrammatically in FIG. 3, further films 15,16 with a printed-on heater 18 were laminated on before heating.

The sensor elements manufactured were incorporated in the sensor housing of the type known from the German Offenlegungsschrift 3,206,903 and 3,537,051 and used to measure the fuel/air ratio in Lean and rich exhaust gases.

We claim:

1. A sensor element formed as a pump cell for limiting current sensor for determining the λ value of lean exhaust gas of an internal combustion engine, comprising one of a planar solid electrolyte and a solid electrolyte in the form of a film, said solid electrolyte conducting $O^{2-}$ ions and being formed with a diffusion channel (7) for the gas under test, an outer pump electrode (9) disposed on the solid electrolyte (5, 6; 13, 14) and connected to a first conductor track (10), and two inner pump electrodes (8, 8') arranged on the solid electrolyte in the diffusion channel (7) opposite the outer pump electrode (9) and on opposite sides of the diffusion channel (7), the inner pump electrodes (8, 8') being directly connected one to another and to a second conductor track (10) extending into the diffusion channel (7).

2. Sensor element according to claim 1, characterized in that the inner pump electrodes (8, 8') are disposed on different ones of said solid electrolytes (5, 6; 13, 14) assembled by a laminating process.

3. Sensor element according to claim 1, characterized in that between the first conductor track (10) and the solid electrolyte an insulating layer (19) is disposed.

4. Sensor element according to claim 2, further comprising a heater (18) contained between two additional solid electrolytes (15, 16) assembled by a lamination process.

5. Sensor element according to claim 1, characterized in that the sensor is manufactured by ceramic-film and screen-printing technology.

6. Sensor element according to claim 1, characterized in that a porous covering layer is disposed above the outer pump electrode (9) and the associated first conductor track (10).

7. Sensor element according to claim 1, characterized in that the inner pump electrodes (8, 8') and the outer pump electrode (9) are annular, and the solid electrolyte is provided with an inlet hole (17) joining the diffusion channel (7) for the gas under test, the inlet hole (17) passing though the inner pump electrodes (8, 8') and the outer pump electrode (9).

8. Sensor element according to claim 1, characterized in that the diffusion channel 7 contains a porous filling which acts as diffusion barrier.

* * * * *